United States Patent
Wang et al.

(10) Patent No.: US 11,512,298 B2
(45) Date of Patent: Nov. 29, 2022

(54) GLUCOAMYLASE MUTANT GA3 WITH IMPROVED SPECIFIC ACTIVITY AND THERMAL STABILITY, AND GENE AND APPLICATION THEREOF

(71) Applicant: Shandong Lonct Enzymes Co. LTD, Linyi (CN)

(72) Inventors: Xingji Wang, Linyi (CN); Kefen Wang, Linyi (CN); Jie Zhang, Linyi (CN); Xinwei Tong, Linyi (CN); Wenlong Liu, Linyi (CN)

(73) Assignee: Shandong Lonct Enzymes Co. LTD, Linyi (CN)

( * ) Notice: Subject to any disclaimer, the term of this patent is extended or adjusted under 35 U.S.C. 154(b) by 0 days.

(21) Appl. No.: 17/169,461

(22) Filed: Feb. 6, 2021

(65) Prior Publication Data
US 2021/0163911 A1    Jun. 3, 2021

(30) Foreign Application Priority Data
Feb. 29, 2020   (CN) .......................... 2020101317423

(51) Int. Cl.
*C12N 9/34*    (2006.01)
(52) U.S. Cl.
CPC .... *C12N 9/2428* (2013.01); *C12Y 302/01003* (2013.01)
(58) Field of Classification Search
CPC .................. C12N 9/2428; C12Y 302/01003
See application file for complete search history.

(56) References Cited

FOREIGN PATENT DOCUMENTS

| CN | 102382807 A | 3/2012 |
| CN | 109385413 A | 2/2019 |

OTHER PUBLICATIONS

Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Yang Jian; Jin Hui; Wang Qingyan; Huang Ribo—"Fusion expression of starch binding domain with αlpha amylase and its properties", Sep. 30, 2010, Chinese J. Bioprocess Eng., 2010, vol. 8(5): 39-43.

* cited by examiner

*Primary Examiner* — Ganapathirama Raghu

(57) ABSTRACT

Glucoamylase mutant GA3 with improved specific activity and thermal stability, and its gene and application are provided, belonging to the field of gene engineering. The glucoamylase mutant GA3 of the present invention obtained by sequentially mutation at fixed points starting from wild glucoamylase processes both improved thermal stability and catalytic efficiency, and can be applied to the industries of feed, food, medicine and the like.

8 Claims, 2 Drawing Sheets
Specification includes a Sequence Listing.

GLUCOAMYLASE MUTANT GA3 WITH IMPROVED SPECIFIC ACTIVITY AND THERMAL STABILITY, AND GENE AND APPLICATION THEREOF

CROSS REFERENCE TO RELATED APPLICATION

The present application is based upon and claims priority to Chinese Application No. 2020101317423, filed on Feb. 29, 2020, and entitled "glucoamylase mutant GA3 with improved specific activity and thermal stability and gene and use thereof", the entire contents of which are incorporated herein by reference.

TECHNICAL FIELD

The present disclosure relates to the field of genetic engineering, in particular to glucoamylase mutant GA3 with improved specific activity and thermal stability and gene and use thereof.

BACKGROUND ART

Amylase is a very versatile biocatalyst, which can be used in breadmaking industry, starch saccharification and liquefaction, textile desizing, papermaking, detergent industry, chemistry, clinical medicine analysis and pharmaceutical industry, etc. The amylase family includes α-amylase, β-amylase and glucoamylase. α-amylase is an endonuclease that acts on the α-1,4 glycosidic bond inside the starch molecule to generate dextrins and oligosaccharides. β-amylase is an exonuclease, which cuts the maltose from starch in a non-reducing form sequentially. Glucoamylase is an exonuclease that acts on the α-1,4 glycosidic bond, with the system name of α-1,4-glucan glucohydrolase (α-1,4-glucan glucohydrolase, EC.3.2.1.3) or γ-amylase (γ-amylase), also referred to as diastatic enzyme. Glucoamylase (diastatic enzyme) cuts the glucose molecule from the terminal of non-reducing sugar. The substrate specificity of glucoamylase is low, that is, it can cut the α-1,4-glycosidic bond, and also has slight hydrolysis ability for α-1,6-glycosidic bond and α-1,3-glycosidic bond. Glucoamylase is one of the most used biological enzyme preparations in industry, which is widely used in food, medicine and fermentation industries. It is one of the largest production and consumption biological enzyme products in China, and has high commercial value.

At present, energy shortage and environmental pollution have greatly restricted the development and progress of society. As an alternative energy source, ethanol has been gradually recognized by people and is considered to be one of the effective ways to solve the above problems. The current methods for producing ethanol from starch include the construction of engineered strains that secrete glucoamylase. Although there are also fermentation production methods using mixed culture of saccharification and fermentation strains to produce ethanol at home and abroad, the disadvantage of this process is that the strain itself needs to consume most of the starch substrate for its growth, and the actual starch utilization rate and ethanol yield are still quite low. Glucoamylase can efficiently degrade α-1,4, α-1,3, and α-1,6-glycosidic bonds, and release glucose from the terminal of non-reducing starch, so it has high commercial value.

Glucoamylase is widely used in industrial production. In the alcohol industry, glucoamylase preparations can replace homemade bran koji, so as to simplify the production process, and improve production efficiency. Therefore, glucoamylase has a wide range of application value in light industry, food, medicine, fermentation and other industries.

SUMMARY OF THE INVENTION

The present disclosure provides glucoamylase mutants with improved specific activity and thermal stability.

The present disclosure also provides the corresponding genes encoding the above glucoamylase mutants.

The present disclosure also provides recombinant vectors comprising the genes encoding the above glucoamylase mutants.

The present disclosure also provides recombinant strains comprising the genes encoding the above glucoamylase mutants.

The present disclosure also provides a method for preparing a glucoamylase mutants.

The present disclosure also provides a use of the above glucoamylase mutants.

According to the embodiments of the present disclosure, the glucoamylase TlGA1931 obtained from strain *Talaromyces leycettanus* JCM12802 is mutated by the inventors to obtain glucoamylase mutants with improved specific activity and thermal stability. The amino acid sequence of the wild-type glucoamylase TlGA1931 is shown in SEQ ID NO:1:

```
  1 MQYLLKTTLG ALSVAQLVIA APHPTELLPR ASGSLDSWLS
 41 TEVPYALDGV LNNIGPNGAK AQGASSGIVV ASPSTSNPDY
 81 FYSWTRDAAL TIKCLIDEFI STGDANLQSV IQNYISSQAF
121 LQTVSNPSGG LSTGGLGEPK FEVNEAAFTG AWGRPQRDGP
161 ALRATAMINY ANWLIANGQA SLANSIVWPI VQNDLSYVSQ
201 YWNQSTFDLW EEIDSSSFFT TAVQHRALVE GSALAKKLGH
241 TCSNCDSQAP LVLCFLQSYW TGSYILSNTG GGRSGKDANS
281 LLGSIHTFDP AAAGCDDTTF QPCSARALAN HKWTDSFRS
321 IYSINSGIPQ GQAVAVGRYP EDVYQGGNAW YLCTLAAAEQ
361 LYDALYQWNR IGSLTITDVS LAFFQDLYPS AATGTYSSSS
401 STYQSIVAAV KTYADGYMSI VQKYTPSNGA LAEQFSRNDG
441 SPLSAVDLTW SYASLLTAAA RRNFSVPAYS WGEASANTVP
481 SSCSASSASG PYATATNTNW PAPTCTSPPA NVAVRFNEMV
521 TTNFGENVFV VGSIAALGSW SPSSAIPLSA AEYNSQTPLW
561 YAIVTLPAGT SFQYKYIKKE PDGSVVWESD PNRSYTVPQG
601 CGVTTATVND SWR*
```

According to the embodiments of the present invention: starting from glucoamylase TlGA1931, the amino acid at position 132 in the amino acid sequence of is mutated from Ser to Cys, the amino acid at position 492 is mutated from Tyr to Cys, the amino acid at position 548 is mutated from Leu to Cys, and the amino acid at position 562 is mutated from Ala to Cys, and a glucoamylase mutant GA1 is obtained; starting from the glucoamylase mutant GA1, the amino acid at position 108 in the amino acid sequence of the mutant GA1 of glucoamylase TlGA1931 is mutated from Gln to Glu, and a glucoamylase mutant GA2 is obtained; then staring from the glucoamylase mutant GA2, the amino acids at positions 468, 469, and 470 in the amino acid sequence of the mutant GA2 of glucoamylase TlGA1931 are mutated from Ala, Tyr, Ser to either Asp or Pro respectively, and a glucoamylase mutant GA3 is obtained.

According to embodiments of the present invention, the amino acid sequence of the mutant GA1 of glucoamylase TlGA1931 is shown in SEQ ID NO: 2:

```
  1 MQYLLKTTLG ALSVAQLVIA APHPTELLPR ASGSLDSWLS
 41 TEVPYALDGV LNNIGPNGAK AQGASSGIVV ASPSTSNPDY
 81 FYSWTRDAAL TIKCLIDEFI STGDANLQSV IQNYISSQAF
121 LQTVSNPSGG LCTGGLGEPK FEVNEAAFTG AWGRPQRDGP
161 ALRATAMINY ANWLIANGQA SLANSIVWPI VQNDLSYVSQ
201 YWNQSTFDLW EEIDSSSFFT TAVQHRALVE GSALAKKLGH
241 TCSNCDSQAP LVLCFLQSYW TGSYILSNTG GGRSGKDANS
281 LLGSIHTFDP AAAGCDDTTF QPCSARALAN HKWTDSFRS
321 IYSINSGIPQ GQAVAVGRYP EDVYQGGNAW YLCTLAAAEQ
361 LYDALYQWNR IGSLTITDVS LAFFQDLYPS AATGTYSSSS
401 STYQSIVAAV KTYADGYMSI VQKYTPSNGA LAEQFSRNDG
441 SPLSAVDLTW SYASLLTAAA RRNFSVPAYS WGEASANTVP
481 SSCSASSASG PCATATNTNW PAPTCTSPPA NVAVRFNEMV
521 TTNFGENVFV VGSIAALGSW SPSSAIPCSA AEYNSQTPLW
561 YCIVTLPAGT SFQYKYIKKE PDGSVVWESD PNRSYTVPQG
601 CGVTTATVND SWR*
```

According to embodiments of the present invention, the amino acid sequence of the mutant GA2 of glucoamylase TlGA1931 is shown in SEQ ID NO: 3:

```
  1 MQYLLKTTLG ALSVAQLVIA APHPTELLPR ASGSLDSWLS
 41 TEVPYALDGV LNNIGPNGAK AQGASSGIVV ASPSTSNPDY
 81 FYSWTRDAAL TIKCLIDEFI STGDANLESV IQNYISSQAF
121 LQTVSNPSGG LCTGGLGEPK FEVNEAAFTG AWGRPQRDGP
161 ALRATAMINY ANWLIANGQA SLANSIVWPI VQNDLSYVSQ
201 YWNQSTFDLW EEIDSSSFFT TAVQHRALVE GSALAKKLGH
241 TCSNCDSQAP LVLCFLQSYW TGSYILSNTG GGRSGKDANS
281 LLGSIHTFDP AAAGCDDTTF QPCSARALAN HKWTDSFRS
321 IYSINSGIPQ GQAVAVGRYP EDVYQGGNAW YLCTLAAAEQ
361 LYDALYQWNR IGSLTITDVS LAFFQDLYPS AATGTYSSSS
401 STYQSIVAAV KTYADGYMSI VQKYTPSNGA LAEQFSRNDG
441 SPLSAVDLTW SYASLLTAAA RRNFSVPAYS WGEASANTVP
481 SSCSASSASG PCATATNTNW PAPTCTSPPA NVAVRFNEMV
521 TTNFGENVFV VGSIAALGSW SPSSAIPCSA AEYNSQTPLW
561 YCIVTLPAGT SFQYKYIKKE PDGSVVWESD PNRSYTVPQG
601 CGVTTATVND SWR*
```

According to a specific embodiments of the present invention, there comprises amino acid mutation at position 468 from Ala to Asp and position 469 from Tyr to Pro and amino acid deletion at position 470 based on the amino acid sequence shown in SEQ ID NO: 3 to obtain the mutant GA3. The amino acid sequence of the mutant GA3 of glucoamylase TlGA1931 is shown in SEQ ID NO: 4:

```
  1 MQYLLKTTLG ALSVAQLVIA APHPTELLPR ASGSLDSWLS
 41 TEVPYALDGV LNNIGPNGAK AQGASSGIVV ASPSTSNPDY
 81 FYSWTRDAAL TIKCLIDEFI STGDANLESV IQNYISSQAF
121 LQTVSNPSGG LCTGGLGEPK FEVNEAAFTG AWGRPQRDGP
161 ALRATAMINY ANWLIANGQA SLANSIVWPI VQNDLSYVSQ
201 YWNQSTFDLW EEIDSSSFFT TAVQHRALVE GSALAKKLGH
241 TCSNCDSQAP LVLCFLQSYW TGSYILSNTG GGRSGKDANS
281 LLGSIHTFDP AAAGCDDTTF QPCSARALAN HKWTDSFRS
321 IYSINSGIPQ GQAVAVGRYP EDVYQGGNAW YLCTLAAAEQ
361 LYDALYQWNR IGSLTITDVS LAFFQDLYPS AATGTYSSSS
401 STYQSIVAAV KTYADGYMSI VQKYTPSNGA LAEQFSRNDG
441 SPLSAVDLTW SYASLLTAAA RRNFSVPDPW GEASANTVPS
481 SCSASSASGP CATATNTNWP APTCTSPPAN VAVRFNEMVT
521 TNFGENVFVV GSIAALGSWS PSSAIPCSAA EYNSQTPLWY
561 CIVTLPAGTS FQYKYIKKEP DGSWWESDP NRSYTVPQGC
601 GVTTATVNDS WR*
```

The present disclosure provides a gene encoding a mutant of the above glucoamylase TlGA1931.

According to a specific embodiment of the present invention, the gene sequence of wild-type glucoamylase TlGA193 is shown in SEQ ID NO: 5:

```
  1 ATGCAGTACC TTCTTAAAAC TACCCTCGGC GCTCTGAGCG TTGCTCAGCT
 51 TGTCATCGCG GCACCACATC CCACGGAACT TCTCCCTCGG GCATCAGGGT
101 CCCTGGATTC ATGGCTTTCC ACCGAAGTTC CTTACGCTCT CGATGGTGTA
151 TTGAACAACA TCGGACCCAA TGGTGCAAAG GCCCAGGGGG CCAGCTCCGG
201 CATTGTGGTT GCAAGCCCCA GCACAAGTAA TCCTGACTAC TTCTACTCTT
251 GGACTCGGGA CGCTGCGCTC ACCATCAAAT GCCTGATCGA TGAGTTCATC
301 TCGACTGGGG ATGCGAACCT GCAGTCGGTG ATTCAGAACT ATATCAGCTC
```

-continued

```
 351 CCAGGCCTTC TTGCAAACAG TGTCCAACCC CTCTGGCGGC CTGTCAACTG

401 GAGGTCTCGG CGAGCCCAAG TTTGAGGTCA ATGAGGCGGC ATTTACTGGT

451 GCTTGGGGCC GGCCACAAAG AGATGGGCCG GCCTTGAGAG CGACTGCCAT

501 GATCAATTAC GCCAACTGGC TTATTGCAAA TGGACAGGCT TCACTCGCCA

551 ATTCGATCGT CTGGCCGATC GTCCAGAATG ATCTCTCCTA CGTCAGCCAG

601 TACTGGAATC AGAGTACCTT TGACCTTTGG GAGGAAATCG ACAGCTCCTC

651 CTTCTTCACG ACGGCTGTGC AGCACCGTGC TCTTGTTGAG GGCTCTGCTC

701 TGGCAAAAAA GCTTGGCCAT ACCTGCTCAA ACTGCGACTC TCAAGCACCG

751 CTTGTCTTGT GTTTCCTGCA ATCCTACTGG ACCGGTTCCT ATATTCTTTC

801 CAACACCGGA GGCGGACGTT CCGGAAAGGA CGCCAACTCC CTACTTGGAA

851 GTATTCATAC TTTTGACCCA GCAGCGGCGG GATGCGACGA CACCACTTTC

901 CAGCCTTGCT CTGCCCGAGC CCTAGCGAAC CACAAGGTCG TCACCGACTC

951 GTTCCGTTCA ATCTACTCAA TCAACTCGGG CATCCCACAG GGCCAAGCAG

1001 TCGCCGTGGG TCGCTACCCT GAAGATGTAT ATCAGGGCGG AAACGCATGG

1051 TATCTCTGCA CCCTCGCTGC TGCAGAGCAG CTGTACGACG CACTCTATCA

1101 GTGGAACAGG ATCGGATCTC TCACGATCAC GGACGTCAGC TTGGCATTCT

1151 TCCAGGATCT CTACCCATCG GCGGCAACAG GCACTTATTC CTCATCCTCG

1201 TCGACCTACC AATCCATCGT TGCCGCTGTC AAGACGTACG CGGACGGATA

1251 CATGAGCATT GTTCAAAAAT ACACCCCTTC CAACGGCGCC CTCGCCGAGC

1301 AGTTCTCCCG CAACGATGGC TCCCCCCTCT CAGCCGTCGA CCTAACCTGG

1351 TCCTACGCCT CCCTGCTCAC TGCCGCCGCG CGCAGAAATT TCTCCGTCCC

1401 CGCCTACTCC TGGGGCGAAG CCAGCGCCAA CACCGTCCCA TCGTCTTGCT

1451 CGGCCTCGTC TGCCTCAGGC CCCTATGCCA CCGCGACCAA CACGAACTGG

1501 CCCGCACCCA CATGCACCTC GCCACCGGCA AACGTGGCCG TCCGATTCAA

1551 CGAGATGGTC ACTACCAACT TTGGAGAGAA CGTCTTTGTC GTGGGCTCGA

1601 TCGCCGCGTT GGGATCTTGG AGTCCTAGTT CCGCTATCCC GCTGAGCGCG

1651 GCCGAATACA ACTCACAGAC GCCGTTGTGG TATGCAATCG TGACGTTGCC

1701 GGCGGGCACG AGCTTCCAGT ATAAGTATAT CAAGAAAGAG CCGGATGGCA

1751 GTGTGGTCTG GGAGAGTGAT CCGAACAGGT CCTATACGGT GCCTCAAGGG

1801 TGTGGCGTGA CGACTGCGAC GGTGAATGAT AGTTGGAGGT AG
```

According to embodiments of the present invention, the gene sequence encoding the mutant GA1 of glucoamylase TlGA1931 is shown in SEQ ID NO: 6:

```
   1 ATGCAGTACC TTCTTAAAAC TACCCTCGGC GCTCTGAGCG TTGCTCAGCT

51 TGTCATCGCG GCACCACATC CCACGGAACT TCTCCCTCGG GCATCAGGGT

101 CCCTGGATTC ATGGCTTTCC ACCGAAGTTC CTTACGCTCT CGATGGTGTA

151 TTGAACAACA TCGGACCCAA TGGTGCAAAG CCCAGGGGG CCAGCTCCGG

201 CATTGTGGTT GCAAGCCCCA GCACAAGTAA TCCTGACTAC TTCTACTCTT

251 GGACTCGGGA CGCTGCGCTC ACCATCAAAT GCCTGATCGA TGAGTTCATC

301 TCGACTGGGG ATGCGAACCT GCAGTCGGTG ATTCAGAACT ATATCAGCTC
```

```
-continued
 351 CCAGGCCTTC TTGCAAACAG TGTCCAACCC CTCTGGCGGC CTGTGTACTG

401 GAGGTCTCGG CGAGCCCAAG TTTGAGGTCA ATGAGGCGGC ATTTACTGGT

451 GCTTGGGGCC GGCCACAAAG AGATGGGCCG GCCTTGAGAG CGACTGCCAT

501 GATCAATTAC GCCAACTGGC TTATTGCAAA TGGACAGGCT TCACTCGCCA

551 ATTCGATCGT CTGGCCGATC GTCCAGAATG ATCTCTCCTA CGTCAGCCAG

601 TACTGGAATC AGAGTACCTT TGACCTTTGG GAGGAAATCG ACAGCTCCTC

651 CTTCTTCACG ACGGCTGTGC AGCACCGTGC TCTTGTTGAG GGCTCTGCTC

701 TGGCAAAAAA GCTTGGCCAT ACCTGCTCAA ACTGCGACTC TCAAGCACCG

751 CTTGTCTTGT GTTTCCTGCA ATCCTACTGG ACCGGTTCCT ATATTCTTTC

801 CAACACCGGA GGCGGACGTT CCGGAAAGGA CGCCAACTCC CTACTTGGAA

851 GTATTCATAC TTTTGACCCA GCAGCGGCGG GATGCGACGA CACCACTTTC

901 CAGCCTTGCT CTGCCCGAGC CCTAGCGAAC CACAAGGTCG TCACCGACTC

951 GTTCCGTTCA ATCTACTCAA TCAACTCGGG CATCCCACAG GGCCAAGCAG

1001 TCGCCGTGGG TCGCTACCCT GAAGATGTAT ATCAGGGCGG AAACGCATGG

1051 TATCTCTGCA CCCTCGCTGC TGCAGAGCAG CTGTACGACG CACTCTATCA

1101 GTGGAACAGG ATCGGATCTC TCACGATCAC GGACGTCAGC TTGGCATTCT

1151 TCCAGGATCT CTACCCATCG GCGGCAACAG GCACTTATTC CTCATCCTCG

1201 TCGACCTACC AATCCATCGT TGCCGCTGTC AAGACGTACG CGGACGGATA

1251 CATGAGCATT GTTCAAAAAT ACACCCCTTC CAACGGCGCC CTCGCCGAGC

1301 AGTTCTCCCG CAACGATGGC TCCCCCCTCT CAGCCGTCGA CCTAACCTGG

1351 TCCTACGCCT CCCTGCTCAC TGCCGCCGCG CGCAGAAATT TCTCCGTCCC

1401 CGCCTACTCC TGGGGCGAAG CCAGCGCCAA CACCGTCCCA TCGTCTTGCT

1451 CGGCCTCGTC TGCCTCAGGC CCCTGTGCCA CCGCGACCAA CACGAACTGG

1501 CCCGCACCCA CATGCACCTC GCCACCGGCA AACGTGGCCG TCCGATTCAA

1551 CGAGATGGTC ACTACCAACT TTGGAGAGAA CGTCTTTGTC GTGGGCTCGA

1601 TCGCCGCGTT GGGATCTTGG AGTCCTAGTT CCGCTATCCC GTGTAGCGCG

1651 GCCGAATACA ACTCACAGAC GCCGTTGTGG TATTGTATCG TGACGTTGCC

1701 GGCGGGCACG AGCTTCCAGT ATAAGTATAT CAAGAAAGAG CCGGATGGCA

1751 GTGTGGTCTG GGAGAGTGAT CCGAACAGGT CCTATACGGT GCCTCAAGGG

1801 TGTGGCGTGA CGACTGCGAC GGTGAATGAT AGTTGGAGGT AG
```

According to embodiments of the present invention, the gene sequence encoding the mutant GA2 of glucoamylase TIGA1931 is shown in SE ID NO: 7:

```
  1 ATGCAGTACC TTCTTAAAAC TACCCTCGGC GCTCTGAGCG TTGCTCAGCT

51 TGTCATCGCG GCACCACATC CCACGGAACT TCTCCCTCGG GCATCAGGGT

101 CCCTGGATTC ATGGCTTTCC ACCGAAGTTC CTTACGCTCT CGATGGTGTA

151 TTGAACAACA TCGGACCCAA TGGTGCAAAG GCCCAGGGGG CCAGCTCCGG

201 CATTGTGGTT GCAAGCCCCA GCACAAGTAA TCCTGACTAC TTCTACTCTT

251 GGACTCGGGA CGCTGCGCTC ACCATCAAAT GCCTGATCGA TGAGTTCATC

301 TCGACTGGGG ATGCGAACCT GGAGTCGGTG ATTCAGAACT ATATCAGCTC
```

-continued

```
 351 CCAGGCCTTC TTGCAAACAG TGTCCAACCC CTCTGGCGGC CTGTGTACTG

401 GAGGTCTCGG CGAGCCCAAG TTTGAGGTCA ATGAGGCGGC ATTTACTGGT

451 GCTTGGGGCC GGCCACAAAG AGATGGGCCG GCCTTGAGAG CGACTGCCAT

501 GATCAATTAC GCCAACTGGC TTATTGCAAA TGGACAGGCT TCACTCGCCA

551 ATTCGATCGT CTGGCCGATC GTCCAGAATG ATCTCTCCTA CGTCAGCCAG

601 TACTGGAATC AGAGTACCTT TGACCTTTGG GAGGAAATCG ACAGCTCCTC

651 CTTCTTCACG ACGGCTGTGC AGCACCGTGC TCTTGTTGAG GGCTCTGCTC

701 TGGCAAAAAA GCTTGGCCAT ACCTGCTCAA ACTGCGACTC TCAAGCACCG

751 CTTGTCTTGT GTTTCCTGCA ATCCTACTGG ACCGGTTCCT ATATTCTTTC

801 CAACACCGGA GGCGGACGTT CCGGAAAGGA CGCCAACTCC CTACTTGGAA

851 GTATTCATAC TTTTGACCCA GCAGCGGCGG GATGCGACGA CACCACTTTC

901 CAGCCTTGCT CTGCCCGAGC CCTAGCGAAC CACAAGGTCG TCACCGACTC

951 GTTCCGTTCA ATCTACTCAA TCAACTCGGG CATCCCACAG GGCCAAGCAG

1001 TCGCCGTGGG TCGCTACCCT GAAGATGTAT ATCAGGGCGG AAACGCATGG

1051 TATCTCTGCA CCCTCGCTGC TGCAGAGCAG CTGTACGACG CACTCTATCA

1101 GTGGAACAGG ATCGGATCTC TCACGATCAC GGACGTCAGC TTGGCATTCT

1151 TCCAGGATCT CTACCCATCG GCGGCAACAG GCACTTATTC CTCATCCTCG

1201 TCGACCTACC AATCCATCGT TGCCGCTGTC AAGACGTACG CGGACGGATA

1251 CATGAGCATT GTTCAAAAAT ACACCCCTTC CAACGGCGCC CTCGCCGAGC

1301 AGTTCTCCCG CAACGATGGC TCCCCCCTCT CAGCCGTCGA CCTAACCTGG

1351 TCCTACGCCT CCCTGCTCAC TGCCGCCGCG CGCAGAAATT TCTCCGTCCC

1401 CGCCTACTCC TGGGGCGAAG CCAGCGCCAA CACCGTCCCA TCGTCTTGCT

1451 CGGCCTCGTC TGCCTCAGGC CCCTGTGCCA CCGCGACCAA CACGAACTGG

1501 CCCGCACCCA CATGCACCTC GCCACCGGCA AACGTGGCCG TCCGATTCAA

1551 CGAGATGGTC ACTACCAACT TTGGAGAGAA CGTCTTTGTC GTGGGCTCGA

1601 TCGCCGCGTT GGGATCTTGG AGTCCTAGTT CCGCTATCCC GTGTAGCGCG

1651 GCCGAATACA ACTCACAGAC GCCGTTGTGG TATTGTATCG TGACGTTGCC

1701 GGCGGGCACG AGCTTCCAGT ATAAGTATAT CAAGAAAGAG CCGGATGGCA

1751 GTGTGGTCTG GGAGAGTGAT CCGAACAGGT CCTATACGGT GCCTCAAGGG

1801 TGTGGCGTGA CGACTGCGAC GGTGAATGAT AGTTGGAGGT AG
```

According to embodiments of the present invention, the gene sequence encoding the mutant GA3 of glucoamylase TlGA1931 is shown in SEQ ID NO: 8:

```
  1 ATGCAGTACC TTCTTAAAAC TACCCTCGGC GCTCTGAGCG TTGCTCAGCT

51 TGTCATCGCG GCACCACATC CCACGGAACT TCTCCCTCGG GCATCAGGGT

101 CCCTGGATTC ATGGCTTTCC ACCGAAGTTC CTTACGCTCT CGATGGTGTA

151 TTGAACAACA TCGGACCCAA TGGTGCAAAG CCCAGGGGG CCAGCTCCGG

201 CATTGTGGTT GCAAGCCCCA GCACAAGTAA TCCTGACTAC TTCTACTCTT

251 GGACTCGGGA CGCTGCGCTC ACCATCAAAT GCCTGATCGA TGAGTTCATC

301 TCGACTGGGG ATGCGAACCT GGAGTCGGTG ATTCAGAACT ATATCAGCTC
```

```
-continued
 351 CCAGGCCTTC TTGCAAACAG TGTCCAACCC CTCTGGCGGC CTGTGTACTG

401 GAGGTCTCGG CGAGCCCAAG TTTGAGGTCA ATGAGGCGGC ATTTACTGGT

451 GCTTGGGGCC GGCCACAAAG AGATGGGCCG GCCTTGAGAG CGACTGCCAT

501 GATCAATTAC GCCAACTGGC TTATTGCAAA TGGACAGGCT TCACTCGCCA

551 ATTCGATCGT CTGGCCGATC GTCCAGAATG ATCTCTCCTA CGTCAGCCAG

601 TACTGGAATC AGAGTACCTT TGACCTTTGG GAGGAAATCG ACAGCTCCTC

651 CTTCTTCACG ACGGCTGTGC AGCACCGTGC TCTTGTTGAG GGCTCTGCTC

701 TGGCAAAAAA GCTTGGCCAT ACCTGCTCAA ACTGCGACTC TCAAGCACCG

751 CTTGTCTTGT GTTTCCTGCA ATCCTACTGG ACCGGTTCCT ATATTCTTTC

801 CAACACCGGA GGCGGACGTT CCGGAAAGGA CGCCAACTCC CTACTTGGAA

851 GTATTCATAC TTTTGACCCA GCAGCGGCGG GATGCGACGA CACCACTTTC

901 CAGCCTTGCT CTGCCCGAGC CCTAGCGAAC CACAAGGTCG TCACCGACTC

951 GTTCCGTTCA ATCTACTCAA TCAACTCGGG CATCCCACAG GGCCAAGCAG

1001 TCGCCGTGGG TCGCTACCCT GAAGATGTAT ATCAGGGCGG AAACGCATGG

1051 TATCTCTGCA CCCTCGCTGC TGCAGAGCAG CTGTACGACG CACTCTATCA

1101 GTGGAACAGG ATCGGATCTC TCACGATCAC GGACGTCAGC TTGGCATTCT

1151 TCCAGGATCT CTACCCATCG GCGGCAACAG GCACTTATTC CTCATCCTCG

1201 TCGACCTACC AATCCATCGT TGCCGCTGTC AAGACGTACG CGGACGGATA

1251 CATGAGCATT GTTCAAAAAT ACACCCCTTC CAACGGCGCC CTCGCCGAGC

1301 AGTTCTCCCG CAACGATGGC TCCCCCCTCT CAGCCGTCGA CCTAACCTGG

1351 TCCTACGCCT CCCTGCTCAC TGCCGCCGCG CGCAGAAATT TCTCCGTCCC

1401 CGATCCATGG GGCGAAGCCA GCGCCAACAC CGTCCCATCG TCTTGCTCGG

1451 CCTCGTCTGC CTCAGGCCCC TGTGCCACCG CGACCAACAC GAACTGGCCC

1501 GCACCCACAT GCACCTCGCC ACCGGCAAAC GTGGCCGTCC GATTCAACGA

1551 GATGGTCACT ACCAACTTTG GAGAGAACGT CTTTGTCGTG GGCTCGATCG

1601 CCGCGTTGGG ATCTTGGAGT CCTAGTTCCG CTATCCCGTG TAGCGCGGCC

1651 GAATACAACT CACAGACGCC GTTGTGGTAT TGTATCGTGA CGTTGCCGGC

1701 GGGCACGAGC TTCCAGTATA AGTATATCAA GAAAGAGCCG GATGGCAGTG

1751 TGGTCTGGGA GAGTGATCCG AACAGGTCCT ATACGGTGCC TCAAGGGTGT

1801 GGCGTGACGA CTGCGACGGT GAATGATAGT TGGAGGTAG
```

The present disclosure provides recombinant vectors comprising the genes encoding the above glucoamylase TlGA1931 mutants.

The present disclosure also provides recombinant strains comprising the genes encoding the glucoamylase TlGA1931 mutants, the preferred strain is *Pichia pastoris* GS115, and the recombinant strains comprising the glucoamylase mutant genes are recombinant *Pichia pastoris* GS115/GA1, GS115/GA2, GS115/GA3, respectively.

According to embodiments of the present invention, a method for preparing the glucoamylase TlGA1931 mutant is as follows:

(1) transforming a host cell with a recombinant vector comprising a gene encoding any of the glucoamylase TlGA1931 mutants described above, to obtain a recombinant strain;

(2) cultivating the recombinant strain to induce expression of the recombinant glucoamylase TlGA1931 mutant;

(3) recovering and purifying the expressed glucoamylase TlGA1931 mutant.

The Beneficial Effects of the Present Disclosure

The glucoamylase mutant GA1 has the specific activity of 806 U/mg, the glucoamylase GA2 has the specific activity of 1054 U/mg, and the glucoamylase GA3 has the specific activity of 1540 U/mg. Compared with the wild-type glucoamylase TlGA1931 (496 U/mg), their specific activities are increased by 62.5%, 112% and 210%, respectively. In terms of specific activity of the present mutants, there is a substantial increase.

After treatment at 70° C. for 10 min, the relative remaining enzyme activity of the wild type is 14%, and the remaining enzyme activities of the glucoamylase mutants GA1, GA2, and GA3 are 70%, 90%, and 86%, respectively.

After treatment at 75° C. for 2 min, the relative remaining enzyme activity of the wild type glucoamylase is 13%, and that of the mutants GA1, GA2, and GA3 are 80%, 95%, and 80%, respectively. And the optimum temperature is 5° C., 10° C. and 10° C. higher than that of the wild type glucoamylase. Therefore, the thermal stability of the glucoamylase mutants are significantly higher.

From mutant GA1 to GA3, their specific activity and thermal stability have been significantly improved. The present invention provides multiple glucoamylase mutants, which have the excellent properties of high catalytic efficiency and thermal stability, so as to fully meet the needs of industrial applications, and to be well applied in the food, medicine, textile and feed industries, with a broad application prospect.

DETAILED DESCRIPTION OF EMBODIMENTS

Test Materials and Reagents

Figure 1:
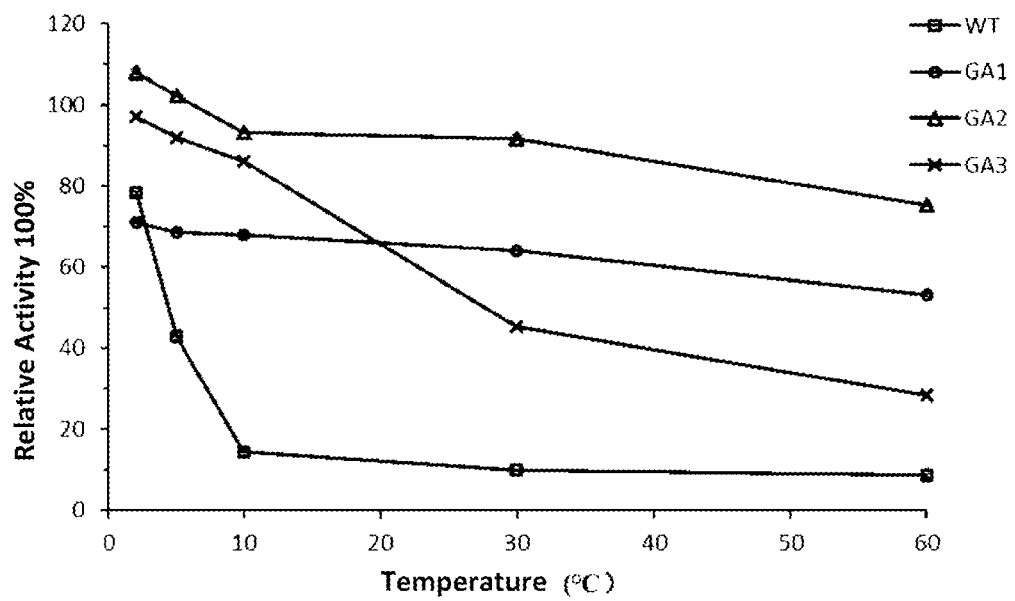
FIG. 1 shows the thermal stability analysis results of glucoamylase mutants GA1 to GA3 of the present disclosure at 70° C.

1. Strains and vectors: *Pichia pastoris* GS115, *Pichia* expression vector pPIC9 and strain GS115.

2. Enzymes and other biochemical reagents: the ligase was purchased from Invitrogen, the site-directed mutagenesis kit was purchased from Quanshijin Company, and the others were domestic reagents (all available from ordinary biochemical reagent companies).

3. Culture Medium:
(1) *E. coli* culture medium LB (1% peptone, 0.5% yeast powder, 1% NaCl, pH 7.0).
(2) BMGY medium: 1% yeast powder, 2% peptone, 1.34% YNB, 0.000049<Biotin, 1% glycerol (v/v).
(3) BMMY medium: replacement of glycerol with 0.5% methanol, and the other components were identical with BMGY medium.

Note: The molecular biology experiment methods that were not specifically explained in the following embodiments were all carried out with reference to the specific methods listed in the "Molecular Cloning Experiment Guide" (Version 3) J. Sambrook, or according to the kit and the product instruction.

Embodiment 1—Site-Directed Mutagenesis of Glucoamylase

Using the glucoamylase TlGA1931 plasmid pPIC9-Tlga1931 sequence as a template, the base at position 132 in the glucoamylase TlGA1931 amino acid sequence was mutated from Ser to Cys, the base at position 492 was mutated from Tyr to Cys, the base at position 548 was mutated from Leu to Cys, the base at position 562 was mutated from Ala to Cys, to obtain a glucoamylase mutant GA1; the base at position 108 in the amino acid sequence of the glucoamylase TlGA1931 mutant GA1 was mutated from Gln to Glu to obtain a glucoamylase Mutant GA2; the bases at positions 468, 469, 470 in the amino acid sequence of the glucoamylase TlGA1931 mutant GA2 were mutated from Ala, Tyr, Ser to either Asp or Pro respectively, to obtain a glucoamylase mutant GA3. The primers for each round of site-directed mutation were shown in the table below:

TABLE 1

Primers required for the experiment

| Primer name | Primer sequence (5'→3')[a] | Primer length (bp) | SEQ ID NO: |
|---|---|---|---|
| S132CF | CTCTGGCGGCCTGTGTACTGGAGGTC | 26 | 9 |
| S132CR | ACACAGGCCGCCAGAGGGGTTGGACAC | 27 | 10 |
| Y492CF | CTGCCTCAGGCCCCTGTGCCACCGCGAC | 28 | 11 |
| Y492CR | ACAGGGGCCTGAGGCAGACGAGGCCGA | 27 | 12 |
| L548CF | AGTTCCGC-TATCCCGTGTAGCGCGGCCGA | 29 | 13 |
| L548CR | ACACGGGATAGCGGAACTAGGACTCCAA | 28 | 14 |
| A562CF | CGCCGTTGTGGTATTGTATCGTGACGTT | 28 | 15 |
| A562CR | ACAATACCACAACGGCGTCTGTGAGTT | 27 | 16 |
| Q108EF | TGGGGATGCGAACCTGGAGTCGGTGAT | 27 | 17 |
| Q108ER | TCCAGGTTCGCATCCCCAGTCGAGAT | 26 | 18 |
| AY5468-470DPF | ATTTCTCCGTCCCCGATC-CATGGGGCGAA | 29 | 19 |
| AYS468-470DPR | ATGGATCGGGGACGGAGAAAT-TTCTGCGC | 29 | 20 |

Embodiment 2 Construction of Glucoamylase Engineering Strain (1) Construction of Expression Vector and Expression in Yeast Using the glucoamylase recombinant plasmid pPIC9-Tlga1931 as a template, the mutant was amplified using site-directed mutagenesis reagents. After verification by nucleic acid gel, 1 μL DMT enzyme was added to the PCR product, mixed and incubated at 37° C. for 1 h. The PCR product digested with 2-5 μL DMT enzyme was transformed by heat shock into competent cell DMT. The positive transformants were selected for DNA sequencing. The transformants with the correct sequence were used to prepare large quantities of recombinant plasmids. Plasmid vector DNA was linearized expressed with restriction enzyme BglII, and yeast GS115 competent cells were transformed by electroporation followed by culture at 30° C. for 2-3 days, then transformants grown on MD plates were picked out for further expression experiments. Please refer to the *Pichia pastoris* expression manual for specific operations. Then the glucoamylase positive clone strains, which were GS115/GA1, GA2, GA3 in sequence, were screened by the color reaction on the MM plate.

Embodiment 3 Preparation of Recombinant Glucoamylase (1) A Large Amount of Glucoamylase Expression in *Pichia pastoris* at Shake Flask Level The transformants with higher enzyme activity were selected and inoculated into 300 mL BMGY liquid medium in a 1 L Erlenmeyer flask, and cultured with shaking at 30° C., 220 rpm for 48 h; centrifuged at 4500 rpm for 5 min followed by discarding the supernatant, and then addition of 200 mL BMMY liquid medium containing 0.5% methanol to the bacteria with induction culture at 30° C. for 48 h. During the induction culture period, methanol solution was added once every 24 h to compensate for the loss of methanol to keep the methanol concentration at about 0.5%; followed by centrifuging at 12,000×g for 10 min, collecting the supernatant fermentation broth, detecting enzyme activity and performing SDS-PAGE protein electrophoresis analysis.

(2) Purification of Recombinant Glucoamylase

The supernatant of recombinant glucoamylase cultured in shake flask fermentation was collected, and the fermentation broth was concentrated using a 10 kDa membrane package. Meanwhile, the medium was replaced with 10 mM disodium hydrogen phosphate-citrate buffer at pH 6.3, followed by passing through an anion exchange column to purify.

Embodiment 4 Determination of the Enzymatic Property of Purified Glucoamylase Mutant The activity of the glucoamylase of the present invention was analyzed by the DNS method. The specific method was as follows:

under the optimal pH and temperature conditions of each mutant (the optimal pH was 4.5, the optimal temperature was GA1-70° C., GA2, GA3-75° C., respectively), 1 mL reaction system including 100 μL of appropriate diluted enzyme solution, 900 μL of substrate was reacted for 30 min, with addition of 1.5 mL DNS to stop the reaction, followed by boiling for 5 min. OD value was measured at 540 nm after cooling. Definition of glucoamylase activity unit: under the corresponding optimal temperature and optimal pH conditions, the amount of enzyme required to catalyze the hydrolysis of substrates and release 1 μmol of reducing sugars per minute was an enzyme activity unit (U).

Identification and Determination of the three glucoamylase mutants GA1, GA2, and GA3 of the present disclosure and their enzyme activity and thermal stability:

1. Determination of the Enzyme Activity of the Three Glucoamylase Mutants GA1, GA2 and GA3.

Each mutant of the purified glucoamylase of the present invention was subjected to an enzymatic reaction at pH 4.5, under 70° C. and 75° C. to determine its enzyme activity.

The glucoamylase mutant GA1 had the specific activity of 806 U/mg, the glucoamylase mutant GA2 had the specific activity of 1054 U/mg, and the glucoamylase mutant GA3 had the specific activity of 1540 U/mg. Compared with the wild-type glucoamylase TlGA1931 (496 U/mg), their specific activities were increased by 62.5%, 112% and 210%, respectively.

2. Determination of the Stability of the Three Glucoamylase Mutants GA1, GA2 and GA3 at 70° C. and 75° C.:

In a 0.1 mol/L citric acid-disodium hydrogen phosphate buffer (pH 6.3) buffer system, glucoamylase mutants GA1, GA2, and GA3 were treated at 70° C. for 0, 2, 5, 10, 20, 30, 60 min, and treated at 75° C. for 0, 2, 5, 10, 20, 30, 60 min, followed by determination of the relative remaining enzyme activity at the corresponding optimum temperature.

As shown in FIG. 1, the relative remaining enzyme activity of the wild type was 14% after being treated at 70° C. for 10 min, which was close to inactivation. The remaining enzyme activities of the modified glucoamylase mutants GA1, GA2, and GA3 were 70%, 90%, 86%, respectively.

Figure 2:
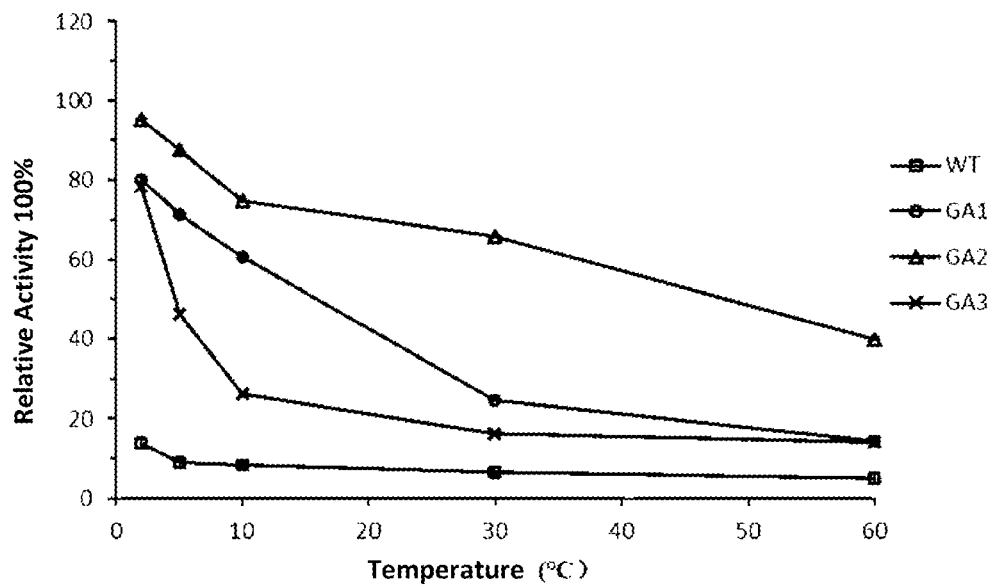
FIG. 2 shows the thermal stability analysis results of glucoamylase mutants GA1 to GA3 of the present disclosure at 75° C.

As shown in FIG. 2, the relative remaining enzyme activity of the wild type after treatment at 75° C. for 2 min was 13%, which was close to inactivation. The remaining enzyme activities of the modified glucoamylase mutants GA1, GA2, and GA3 were 80%, 95%, 80%, respectively.

Figure 3:
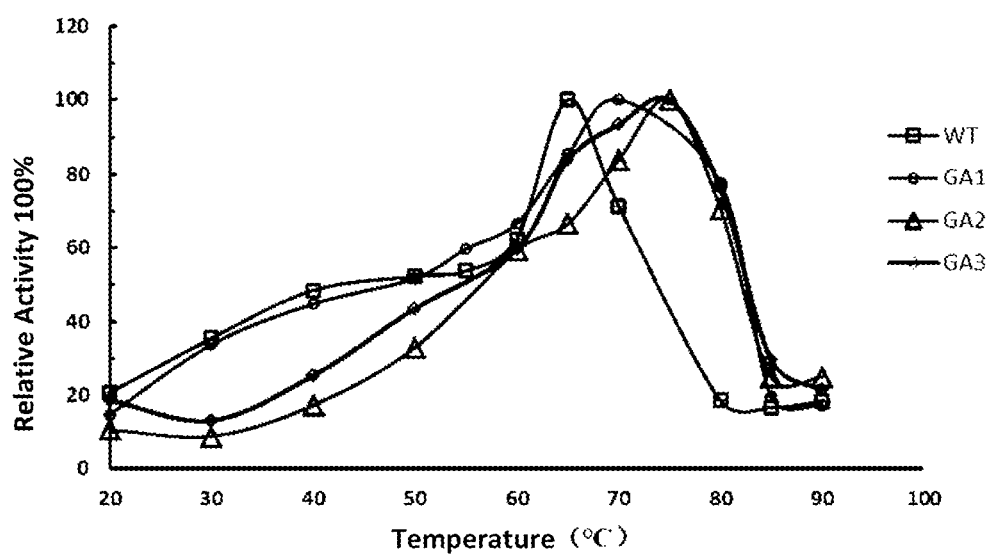
FIG. 3 shows the analysis results of glucoamylase mutants GA1 to GA3 of the present disclosure at the optimum temperature.

3. Determination of the Optimum Temperature:

The three mutants of glucoamylase GA1, GA2, GA3 were tested for their enzyme activity at 20, 30, 40, 50, 55, 60, 65, 70, 80, 85, 90° C. and pH 4.5, respectively. As shown in FIG. 3, the optimum temperature for glucoamylase mutants GA1, GA2, and GA3 were 70° C., 75° C., and 75° C., respectively.

4. The Optimum pH and pH Stability of the Three Mutants of Glucoamylase GA1, GA2 and GA3 were Substantially Consistent with Those of the Wild Type.

We claim:

1. A glucoamylase mutant GA3 with improved specific activity and thermal stability, the amino acid sequence is set forth in SEQ ID NO: 4.

2. A method for preparing the glucoamylase mutant GA3 with improved specific activity and thermal stability of claim 1, comprising steps of:
   (1) performing mutation based on glucoamylase TlGA1931, mutating the amino acid residue at position 132 in the amino acid sequence from Ser to Cys, the amino acid residue at position 492 from Tyr to Cys, the amino acid residue at position 548 from Leu to Cys, and the amino acid residue at position 562 from Ala to Cys, to obtain a glucoamylase mutant GA1 of glucoamylase TlGA1931, wherein the amino acid sequence of glucoamylase TlGA1931 is set forth in SEQ ID NO.1;
   (2) performing mutation based on the glucoamylase mutant GA1, mutating the amino acid residue at position 108 in the amino acid sequence from Gln to Glu, to obtain a glucoamylase mutant GA2;
   (3) performing mutation based on the glucoamylase mutant GA2, mutating amino acids at position 468 from Ala to Asp, position 469 from Tyr to Pro and omitting the amino acid at position 470 respectively, to obtain the glucoamylase mutant GA3.

3. A glucoamylase mutant gene encoding the glucoamylase mutant GA3 with improved specific activity and thermal stability of claim 1.

4. The glucoamylase mutant gene according to claim 3, the nucleotide sequence is set forth in SEQ ID NO: 8.

5. A recombinant vector comprising the glucoamylase mutant gene of claim 3.

6. An isolated recombinant host cell comprising the glucoamylase mutant gene of claim 3.

7. A method for preparing a glucoamylase with improved specific activity and thermal stability using the glucoamylase mutant GA3 of claim 1, comprising steps of:
   (1) transforming a host cell with a recombinant vector comprising a gene encoding the glucoamylase mutant GA3 of claim 1, to obtain a recombinant strain;
   (2) cultivating the recombinant strain to induce expression of the glucoamylase mutant;

(3) recovering and purifying the expressed mutant glucoamylase, to prepare a glucoamylase with improved specific activity and thermal stability.

8. A method of applying the glucoamylase mutant GA3 of claim 1 for preparing a glucoamylase with improved specific activity and thermal stability.

* * * * *

SEQUENCE LISTING

<160> NUMBER OF SEQ ID NOS: 20

<210> SEQ ID NO 1
<211> LENGTH: 613
<212> TYPE: PRT
<213> ORGANISM: Talaromyces leycettanusJCM12802

<400> SEQUENCE: 1

```
Met Gln Tyr Leu Leu Lys Thr Thr Leu Gly Ala Leu Ser Val Ala Gln
1               5                   10                  15

Leu Val Ile Ala Ala Pro His Pro Thr Glu Leu Leu Pro Arg Ala Ser
            20                  25                  30

Gly Ser Leu Asp Ser Trp Leu Ser Thr Glu Val Pro Tyr Ala Leu Asp
        35                  40                  45

Gly Val Leu Asn Asn Ile Gly Pro Asn Gly Ala Lys Ala Gln Gly Ala
    50                  55                  60
```

-continued

```
Ser Ser Gly Ile Val Val Ala Ser Pro Ser Thr Ser Asn Pro Asp Tyr
 65                  70                  75                  80

Phe Tyr Ser Trp Thr Arg Asp Ala Ala Leu Thr Ile Lys Cys Leu Ile
                 85                  90                  95

Asp Glu Phe Ile Ser Thr Gly Asp Ala Asn Leu Gln Ser Val Ile Gln
            100                 105                 110

Asn Tyr Ile Ser Ser Gln Ala Phe Leu Gln Thr Val Ser Asn Pro Ser
        115                 120                 125

Gly Gly Leu Ser Thr Gly Leu Gly Glu Pro Lys Phe Glu Val Asn
    130                 135                 140

Glu Ala Ala Phe Thr Gly Ala Trp Gly Arg Pro Gln Arg Asp Gly Pro
145                 150                 155                 160

Ala Leu Arg Ala Thr Ala Met Ile Asn Tyr Ala Asn Trp Leu Ile Ala
                165                 170                 175

Asn Gly Gln Ala Ser Leu Ala Asn Ser Ile Val Trp Pro Ile Val Gln
            180                 185                 190

Asn Asp Leu Ser Tyr Val Ser Gln Tyr Trp Asn Gln Ser Thr Phe Asp
        195                 200                 205

Leu Trp Glu Glu Ile Asp Ser Ser Phe Thr Thr Ala Val Gln
    210                 215                 220

His Arg Ala Leu Val Glu Gly Ser Ala Leu Ala Lys Lys Leu Gly His
225                 230                 235                 240

Thr Cys Ser Asn Cys Asp Ser Gln Ala Pro Leu Val Leu Cys Phe Leu
                245                 250                 255

Gln Ser Tyr Trp Thr Gly Ser Tyr Ile Leu Ser Asn Thr Gly Gly Gly
            260                 265                 270

Arg Ser Gly Lys Asp Ala Asn Ser Leu Leu Gly Ser Ile His Thr Phe
        275                 280                 285

Asp Pro Ala Ala Ala Gly Cys Asp Asp Thr Thr Phe Gln Pro Cys Ser
    290                 295                 300

Ala Arg Ala Leu Ala Asn His Lys Val Val Thr Asp Ser Phe Arg Ser
305                 310                 315                 320

Ile Tyr Ser Ile Asn Ser Gly Ile Pro Gln Gly Gln Ala Val Ala Val
                325                 330                 335

Gly Arg Tyr Pro Glu Asp Val Tyr Gln Gly Gly Asn Ala Trp Tyr Leu
            340                 345                 350

Cys Thr Leu Ala Ala Ala Glu Gln Leu Tyr Asp Ala Leu Tyr Gln Trp
        355                 360                 365

Asn Arg Ile Gly Ser Leu Thr Ile Thr Asp Val Ser Leu Ala Phe Phe
    370                 375                 380

Gln Asp Leu Tyr Pro Ser Ala Ala Thr Gly Thr Tyr Ser Ser Ser Ser
385                 390                 395                 400

Ser Thr Tyr Gln Ser Ile Val Ala Ala Val Lys Thr Tyr Ala Asp Gly
                405                 410                 415

Tyr Met Ser Ile Val Gln Lys Tyr Thr Pro Ser Asn Gly Ala Leu Ala
            420                 425                 430

Glu Gln Phe Ser Arg Asn Asp Gly Ser Pro Leu Ser Ala Val Asp Leu
        435                 440                 445

Thr Trp Ser Tyr Ala Ser Leu Leu Thr Ala Ala Arg Arg Asn Phe
    450                 455                 460

Ser Val Pro Ala Tyr Ser Trp Gly Glu Ala Ser Ala Asn Thr Val Pro
465                 470                 475                 480
```

-continued

```
Ser Ser Cys Ser Ala Ser Ala Ser Gly Pro Tyr Ala Thr Ala Thr
            485                 490                 495

Asn Thr Asn Trp Pro Ala Pro Thr Cys Thr Ser Pro Ala Asn Val
        500                 505                 510

Ala Val Arg Phe Asn Glu Met Val Thr Thr Asn Phe Gly Glu Asn Val
        515                 520                 525

Phe Val Val Gly Ser Ile Ala Ala Leu Gly Ser Trp Ser Pro Ser Ser
    530                 535                 540

Ala Ile Pro Leu Ser Ala Glu Tyr Asn Ser Gln Thr Pro Leu Trp
545                 550                 555                 560

Tyr Ala Ile Val Thr Leu Pro Ala Gly Thr Ser Phe Gln Tyr Lys Tyr
                565                 570                 575

Ile Lys Lys Glu Pro Asp Gly Ser Val Val Trp Glu Ser Asp Pro Asn
        580                 585                 590

Arg Ser Tyr Thr Val Pro Gln Gly Cys Gly Val Thr Thr Ala Thr Val
        595                 600                 605

Asn Asp Ser Trp Arg
        610
```

<210> SEQ ID NO 2
<211> LENGTH: 613
<212> TYPE: PRT
<213> ORGANISM: Artificial Sequence
<220> FEATURE:
<223> OTHER INFORMATION: The sequence is synthesized.

<400> SEQUENCE: 2

```
Met Gln Tyr Leu Leu Lys Thr Thr Leu Gly Ala Leu Ser Val Ala Gln
1               5                   10                  15

Leu Val Ile Ala Ala Pro His Pro Thr Glu Leu Leu Pro Arg Ala Ser
            20                  25                  30

Gly Ser Leu Asp Ser Trp Leu Ser Thr Glu Val Pro Tyr Ala Leu Asp
        35                  40                  45

Gly Val Leu Asn Asn Ile Gly Pro Asn Gly Ala Lys Ala Gln Gly Ala
    50                  55                  60

Ser Ser Gly Ile Val Val Ala Ser Pro Ser Thr Ser Asn Pro Asp Tyr
65                  70                  75                  80

Phe Tyr Ser Trp Thr Arg Asp Ala Ala Leu Thr Ile Lys Cys Leu Ile
                85                  90                  95

Asp Glu Phe Ile Ser Thr Gly Asp Ala Asn Leu Gln Ser Val Ile Gln
            100                 105                 110

Asn Tyr Ile Ser Ser Gln Ala Phe Leu Gln Thr Val Ser Asn Pro Ser
        115                 120                 125

Gly Gly Leu Cys Thr Gly Gly Leu Gly Glu Pro Lys Phe Glu Val Asn
    130                 135                 140

Glu Ala Ala Phe Thr Gly Ala Trp Gly Arg Pro Gln Arg Asp Gly Pro
145                 150                 155                 160

Ala Leu Arg Ala Thr Ala Met Ile Asn Tyr Ala Asn Trp Leu Ile Ala
                165                 170                 175

Asn Gly Gln Ala Ser Leu Ala Asn Ser Ile Val Trp Pro Ile Val Gln
            180                 185                 190

Asn Asp Leu Ser Tyr Val Ser Gln Tyr Trp Asn Gln Ser Thr Phe Asp
        195                 200                 205

Leu Trp Glu Glu Ile Asp Ser Ser Phe Phe Thr Thr Ala Val Gln
    210                 215                 220
```

-continued

```
His Arg Ala Leu Val Glu Gly Ser Ala Leu Ala Lys Lys Leu Gly His
225                 230                 235                 240

Thr Cys Ser Asn Cys Asp Ser Gln Ala Pro Leu Val Leu Cys Phe Leu
            245                 250                 255

Gln Ser Tyr Trp Thr Gly Ser Tyr Ile Leu Ser Asn Thr Gly Gly Gly
        260                 265                 270

Arg Ser Gly Lys Asp Ala Asn Ser Leu Leu Gly Ser Ile His Thr Phe
    275                 280                 285

Asp Pro Ala Ala Ala Gly Cys Asp Asp Thr Thr Phe Gln Pro Cys Ser
290                 295                 300

Ala Arg Ala Leu Ala Asn His Lys Val Val Thr Asp Ser Phe Arg Ser
305                 310                 315                 320

Ile Tyr Ser Ile Asn Ser Gly Ile Pro Gln Gly Gln Ala Val Ala Val
            325                 330                 335

Gly Arg Tyr Pro Glu Asp Val Tyr Gln Gly Gly Asn Ala Trp Tyr Leu
        340                 345                 350

Cys Thr Leu Ala Ala Ala Glu Gln Leu Tyr Asp Ala Leu Tyr Gln Trp
    355                 360                 365

Asn Arg Ile Gly Ser Leu Thr Ile Thr Asp Val Ser Leu Ala Phe Phe
370                 375                 380

Gln Asp Leu Tyr Pro Ser Ala Thr Gly Thr Tyr Ser Ser Ser Ser Ser
385                 390                 395                 400

Ser Thr Tyr Gln Ser Ile Val Ala Ala Val Lys Thr Tyr Ala Asp Gly
            405                 410                 415

Tyr Met Ser Ile Val Gln Lys Tyr Thr Pro Ser Asn Gly Ala Leu Ala
        420                 425                 430

Glu Gln Phe Ser Arg Asn Asp Gly Ser Pro Leu Ser Ala Val Asp Leu
    435                 440                 445

Thr Trp Ser Tyr Ala Ser Leu Leu Thr Ala Ala Ala Arg Arg Asn Phe
450                 455                 460

Ser Val Pro Ala Tyr Ser Trp Gly Glu Ala Ser Ala Asn Thr Val Pro
465                 470                 475                 480

Ser Ser Cys Ser Ala Ser Ser Ala Ser Gly Pro Cys Ala Thr Ala Thr
            485                 490                 495

Asn Thr Asn Trp Pro Ala Pro Thr Cys Thr Ser Pro Ala Asn Val
        500                 505                 510

Ala Val Arg Phe Asn Glu Met Val Thr Thr Asn Phe Gly Glu Asn Val
    515                 520                 525

Phe Val Val Gly Ser Ile Ala Ala Leu Gly Ser Trp Ser Pro Ser Ser
530                 535                 540

Ala Ile Pro Cys Ser Ala Glu Tyr Asn Ser Gln Thr Pro Leu Trp
545                 550                 555                 560

Tyr Cys Ile Val Thr Leu Pro Ala Gly Thr Ser Phe Gln Tyr Lys Tyr
            565                 570                 575

Ile Lys Lys Glu Pro Asp Gly Ser Val Val Trp Glu Ser Asp Pro Asn
        580                 585                 590

Arg Ser Tyr Thr Val Pro Gln Gly Cys Gly Val Thr Thr Ala Thr Val
    595                 600                 605

Asn Asp Ser Trp Arg
    610
```

<210> SEQ ID NO 3
<211> LENGTH: 613
<212> TYPE: PRT
<213> ORGANISM: Artificial Sequence
<220> FEATURE:
<223> OTHER INFORMATION: The sequence is synthesized.

<400> SEQUENCE: 3

```
Met Gln Tyr Leu Leu Lys Thr Thr Leu Gly Ala Leu Ser Val Ala Gln
1               5                   10                  15

Leu Val Ile Ala Ala Pro His Pro Thr Glu Leu Leu Pro Arg Ala Ser
            20                  25                  30

Gly Ser Leu Asp Ser Trp Leu Ser Thr Glu Val Pro Tyr Ala Leu Asp
        35                  40                  45

Gly Val Leu Asn Asn Ile Gly Pro Asn Gly Ala Lys Ala Gln Gly Ala
    50                  55                  60

Ser Ser Gly Ile Val Val Ala Ser Pro Ser Thr Ser Asn Pro Asp Tyr
65                  70                  75                  80

Phe Tyr Ser Trp Thr Arg Asp Ala Ala Leu Thr Ile Lys Cys Leu Ile
                85                  90                  95

Asp Glu Phe Ile Ser Thr Gly Asp Ala Asn Leu Glu Ser Val Ile Gln
            100                 105                 110

Asn Tyr Ile Ser Ser Gln Ala Phe Leu Gln Thr Val Ser Asn Pro Ser
        115                 120                 125

Gly Gly Leu Cys Thr Gly Gly Leu Gly Glu Pro Lys Phe Glu Val Asn
    130                 135                 140

Glu Ala Ala Phe Thr Gly Ala Trp Gly Arg Pro Gln Arg Asp Gly Pro
145                 150                 155                 160

Ala Leu Arg Ala Thr Ala Met Ile Asn Tyr Ala Asn Trp Leu Ile Ala
                165                 170                 175

Asn Gly Gln Ala Ser Leu Ala Asn Ser Ile Val Trp Pro Ile Val Gln
            180                 185                 190

Asn Asp Leu Ser Tyr Val Ser Gln Tyr Trp Asn Gln Ser Thr Phe Asp
        195                 200                 205

Leu Trp Glu Glu Ile Asp Ser Ser Phe Phe Thr Thr Ala Val Gln
    210                 215                 220

His Arg Ala Leu Val Glu Gly Ser Ala Leu Ala Lys Lys Leu Gly His
225                 230                 235                 240

Thr Cys Ser Asn Cys Asp Ser Gln Ala Pro Leu Val Leu Cys Phe Leu
                245                 250                 255

Gln Ser Tyr Trp Thr Gly Ser Tyr Ile Leu Ser Asn Thr Gly Gly Gly
            260                 265                 270

Arg Ser Gly Lys Asp Ala Asn Ser Leu Leu Gly Ser Ile His Thr Phe
        275                 280                 285

Asp Pro Ala Ala Ala Gly Cys Asp Asp Thr Thr Phe Gln Pro Cys Ser
    290                 295                 300

Ala Arg Ala Leu Ala Asn His Lys Val Val Thr Asp Ser Phe Arg Ser
305                 310                 315                 320

Ile Tyr Ser Ile Asn Ser Gly Ile Pro Gln Gly Gln Ala Val Ala Val
                325                 330                 335

Gly Arg Tyr Pro Glu Asp Val Tyr Gln Gly Gly Asn Ala Trp Tyr Leu
            340                 345                 350

Cys Thr Leu Ala Ala Ala Glu Gln Leu Tyr Asp Ala Leu Tyr Gln Trp
        355                 360                 365
```

Asn Arg Ile Gly Ser Leu Thr Ile Thr Asp Val Ser Leu Ala Phe Phe
    370                 375                 380

Gln Asp Leu Tyr Pro Ser Ala Ala Thr Gly Thr Tyr Ser Ser Ser Ser
385                 390                 395                 400

Ser Thr Tyr Gln Ser Ile Val Ala Ala Val Lys Thr Tyr Ala Asp Gly
                405                 410                 415

Tyr Met Ser Ile Val Gln Lys Tyr Thr Pro Ser Asn Gly Ala Leu Ala
            420                 425                 430

Glu Gln Phe Ser Arg Asn Asp Gly Ser Pro Leu Ser Ala Val Asp Leu
        435                 440                 445

Thr Trp Ser Tyr Ala Ser Leu Leu Thr Ala Ala Arg Arg Asn Phe
450                 455                 460

Ser Val Pro Ala Tyr Ser Trp Gly Glu Ala Ser Ala Asn Thr Val Pro
465                 470                 475                 480

Ser Ser Cys Ser Ala Ser Ser Ala Ser Gly Pro Cys Ala Thr Ala Thr
                485                 490                 495

Asn Thr Asn Trp Pro Ala Pro Thr Cys Thr Ser Pro Ala Asn Val
            500                 505                 510

Ala Val Arg Phe Asn Glu Met Val Thr Thr Asn Phe Gly Glu Asn Val
        515                 520                 525

Phe Val Val Gly Ser Ile Ala Ala Leu Gly Ser Trp Ser Pro Ser Ser
530                 535                 540

Ala Ile Pro Cys Ser Ala Glu Tyr Asn Ser Gln Thr Pro Leu Trp
545                 550                 555                 560

Tyr Cys Ile Val Thr Leu Pro Ala Gly Thr Ser Phe Gln Tyr Lys Tyr
                565                 570                 575

Ile Lys Lys Glu Pro Asp Gly Ser Val Val Trp Glu Ser Asp Pro Asn
            580                 585                 590

Arg Ser Tyr Thr Val Pro Gln Gly Cys Gly Val Thr Thr Ala Thr Val
        595                 600                 605

Asn Asp Ser Trp Arg
    610

<210> SEQ ID NO 4
<211> LENGTH: 612
<212> TYPE: PRT
<213> ORGANISM: Artificial Sequence
<220> FEATURE:
<223> OTHER INFORMATION: The sequence is synthesized.

<400> SEQUENCE: 4

Met Gln Tyr Leu Leu Lys Thr Thr Leu Gly Ala Leu Ser Val Ala Gln
1               5                   10                  15

Leu Val Ile Ala Ala Pro His Pro Thr Glu Leu Leu Pro Arg Ala Ser
            20                  25                  30

Gly Ser Leu Asp Ser Trp Leu Ser Thr Glu Val Pro Tyr Ala Leu Asp
        35                  40                  45

Gly Val Leu Asn Asn Ile Gly Pro Asn Gly Ala Lys Ala Gln Gly Ala
    50                  55                  60

Ser Ser Gly Ile Val Val Ala Pro Ser Thr Ser Asn Pro Asp Tyr
65                  70                  75                  80

Phe Tyr Ser Trp Thr Arg Asp Ala Ala Leu Thr Ile Lys Cys Leu Ile
                85                  90                  95

Asp Glu Phe Ile Ser Thr Gly Asp Ala Asn Leu Glu Ser Val Ile Gln
            100                 105                 110

```
Asn Tyr Ile Ser Ser Gln Ala Phe Leu Gln Thr Val Ser Asn Pro Ser
            115                 120                 125

Gly Gly Leu Cys Thr Gly Leu Gly Glu Pro Lys Phe Glu Val Asn
130                 135                 140

Glu Ala Ala Phe Thr Gly Ala Trp Gly Arg Pro Gln Arg Asp Gly Pro
145                 150                 155                 160

Ala Leu Arg Ala Thr Ala Met Ile Asn Tyr Ala Asn Trp Leu Ile Ala
                165                 170                 175

Asn Gly Gln Ala Ser Leu Ala Asn Ser Ile Val Trp Pro Ile Val Gln
            180                 185                 190

Asn Asp Leu Ser Tyr Val Ser Gln Tyr Trp Asn Gln Ser Thr Phe Asp
        195                 200                 205

Leu Trp Glu Glu Ile Asp Ser Ser Phe Phe Thr Thr Ala Val Gln
210                 215                 220

His Arg Ala Leu Val Glu Gly Ser Ala Leu Ala Lys Lys Leu Gly His
225                 230                 235                 240

Thr Cys Ser Asn Cys Asp Ser Gln Ala Pro Leu Val Leu Cys Phe Leu
                245                 250                 255

Gln Ser Tyr Trp Thr Gly Ser Tyr Ile Leu Ser Asn Thr Gly Gly Gly
            260                 265                 270

Arg Ser Gly Lys Asp Ala Asn Ser Leu Leu Gly Ser Ile His Thr Phe
        275                 280                 285

Asp Pro Ala Ala Ala Gly Cys Asp Asp Thr Thr Phe Gln Pro Cys Ser
290                 295                 300

Ala Arg Ala Leu Ala Asn His Lys Val Val Thr Asp Ser Phe Arg Ser
305                 310                 315                 320

Ile Tyr Ser Ile Asn Ser Gly Ile Pro Gln Gly Gln Ala Val Ala Val
                325                 330                 335

Gly Arg Tyr Pro Glu Asp Val Tyr Gln Gly Gly Asn Ala Trp Tyr Leu
            340                 345                 350

Cys Thr Leu Ala Ala Ala Glu Gln Leu Tyr Asp Ala Leu Tyr Gln Trp
        355                 360                 365

Asn Arg Ile Gly Ser Leu Thr Ile Thr Asp Val Ser Leu Ala Phe Phe
370                 375                 380

Gln Asp Leu Tyr Pro Ser Ala Ala Thr Gly Thr Tyr Ser Ser Ser Ser
385                 390                 395                 400

Ser Thr Tyr Gln Ser Ile Val Ala Ala Val Lys Thr Tyr Ala Asp Gly
                405                 410                 415

Tyr Met Ser Ile Val Gln Lys Tyr Thr Pro Ser Asn Gly Ala Leu Ala
            420                 425                 430

Glu Gln Phe Ser Arg Asn Asp Gly Ser Pro Leu Ser Ala Val Asp Leu
        435                 440                 445

Thr Trp Ser Tyr Ala Ser Leu Leu Thr Ala Ala Arg Arg Asn Phe
450                 455                 460

Ser Val Pro Asp Pro Trp Gly Glu Ala Ser Ala Asn Thr Val Pro Ser
465                 470                 475                 480

Ser Cys Ser Ala Ser Ser Ala Ser Gly Pro Cys Ala Thr Ala Thr Asn
                485                 490                 495

Thr Asn Trp Pro Ala Pro Thr Cys Thr Ser Pro Pro Ala Asn Val Ala
            500                 505                 510

Val Arg Phe Asn Glu Met Val Thr Thr Asn Phe Gly Glu Asn Val Phe
        515                 520                 525
```

```
Val Val Gly Ser Ile Ala Ala Leu Gly Ser Trp Ser Pro Ser Ser Ala
        530                 535                 540

Ile Pro Cys Ser Ala Ala Glu Tyr Asn Ser Gln Thr Pro Leu Trp Tyr
545                 550                 555                 560

Cys Ile Val Thr Leu Pro Ala Gly Thr Ser Phe Gln Tyr Lys Tyr Ile
                565                 570                 575

Lys Lys Glu Pro Asp Gly Ser Val Val Trp Glu Ser Asp Pro Asn Arg
                580                 585                 590

Ser Tyr Thr Val Pro Gln Gly Cys Gly Val Thr Ala Thr Val Asn
                595                 600                 605

Asp Ser Trp Arg
    610

<210> SEQ ID NO 5
<211> LENGTH: 1842
<212> TYPE: DNA
<213> ORGANISM: Talaromyces leycettanusJCM12802

<400> SEQUENCE: 5
```

| | | | |
|---|---|---|---|
| atgcagtacc ttcttaaaac taccctcggc gctctgagcg ttgctcagct tgtcatcgcg | | | 60 |
| gcaccacatc ccacggaact tctccctcgg catcagggt ccctggattc atggctttcc | | | 120 |
| accgaagttc cttacgctct cgatggtgta ttgaacaaca tcggaccaa tggtgcaaag | | | 180 |
| gcccaggggg ccagctccgg cattgtggtt gcaagcccca gcacaagtaa tcctgactac | | | 240 |
| ttctactctt ggactcggga cgctgcgctc accatcaaat gcctgatcga tgagttcatc | | | 300 |
| tcgactggga tgcgaacct gcagtcggtg attcagaact atatcagctc ccaggccttc | | | 360 |
| ttgcaaacag tgtccaaccc ctctggcggc ctgtcaactg gaggtctcgg cgagcccaag | | | 420 |
| tttgaggtca atgaggcggc atttactggt gcttggggcc ggccacaaag agatgggccg | | | 480 |
| gccttgagag cgactgccat gatcaattac gccaactggc ttattgcaaa tggacaggct | | | 540 |
| tcactcgcca attcgatcgt ctggccgatc gtccagaatg atctctccta cgtcagccag | | | 600 |
| tactggaatc agagtaccct tgaccttgg gaggaaatcg acagctcctc cttcttcacg | | | 660 |
| acggctgtgc agcaccgtgc tcttgttgag ggctctgctc tggcaaaaaa gcttggccat | | | 720 |
| acctgctcaa actgcgactc tcaagcaccg cttgtcttgt gtttcctgca atcctactgg | | | 780 |
| accggttcct atattccttc caacaccgga ggcggacgtt ccggaaagga cgccaactcc | | | 840 |
| ctacttggaa gtattcatac ttttgaccca gcagcggcgg gatgcgacga caccactttc | | | 900 |
| cagccttgct ctgcccgagc cctagcgaac cacaaggtcg tcaccgactc gttccgttca | | | 960 |
| atctactcaa tcaactcggg catcccacag ggccaagcag tcgccgtggg tcgctaccct | | | 1020 |
| gaagatgtat atcagggcgg aaacgcatgg tatctctgca ccctcgctgc tgcagagcag | | | 1080 |
| ctgtacgacg cactctatca gtggaacagg atcggatctc tcacgatcac ggacgtcagc | | | 1140 |
| ttggcattct tccaggatct ctacccatcg gcggcaacag gcacttattc ctcatcctcg | | | 1200 |
| tcgacctacc aatccatcgt tgccgctgtc aagacgtacg cggacggata catgagcatt | | | 1260 |
| gttcaaaaat acaccccttc caacggcgcc ctcgccgagc agttctcccg caacgatggc | | | 1320 |
| tcccccctct cagccgtcga cctaacctgg tcctacgcct ccctgctcac tgccgccgcg | | | 1380 |
| cgcagaaatt tctccgtccc cgcctactcc tggggcgaag ccagcgccaa caccgtccca | | | 1440 |
| tcgtcttgct cggcctcgtc tgcctcaggc ccctatgcca ccgcgaccaa cacgaactgg | | | 1500 |
| cccgcaccca catgcacctc gccaccggca aacgtggccg tccgattcaa cgagatggtc | | | 1560 |
| actaccaact ttggagagaa cgtctttgtc gtgggctcga tcgccgcgtt gggatcttgg | | | 1620 |

| | |
|---|---:|
| agtcctagtt ccgctatccc gctgagcgcg gccgaataca actcacagac gccgttgtgg | 1680 |
| tatgcaatcg tgacgttgcc ggcgggcacg agcttccagt ataagtatat caagaaagag | 1740 |
| ccggatggca gtgtggtctg ggagagtgat ccgaacaggt cctatacggt gcctcaaggg | 1800 |
| tgtggcgtga cgactgcgac ggtgaatgat agttggaggt ag | 1842 |

```
<210> SEQ ID NO 6
<211> LENGTH: 1842
<212> TYPE: DNA
<213> ORGANISM: Artificial Sequence
<220> FEATURE:
<223> OTHER INFORMATION: The sequence is synthesized.

<400> SEQUENCE: 6
```

| | |
|---|---:|
| atgcagtacc ttcttaaaac taccctcggc gctctgagcg ttgctcagct tgtcatcgcg | 60 |
| gcaccacatc ccacggaact tctccctcgg gcatcagggt ccctggattc atggctttcc | 120 |
| accgaagttc cttacgctct cgatggtgta ttgaacaaca tcggacccaa tggtgcaaag | 180 |
| gcccaggggg ccagctccgg cattgtggtt gcaagcccca gcacaagtaa tcctgactac | 240 |
| ttctactctt ggactcggga cgctgcgctc accatcaaat gcctgatcga tgagttcatc | 300 |
| tcgactgggg atgcgaacct gcagtcggtg attcagaact atatcagctc ccaggccttc | 360 |
| ttgcaaacag tgtccaaccc ctctggcggc ctgtgtactg gaggtctcgg cgagcccaag | 420 |
| tttgaggtca atgaggcggc atttactggt gcttggggcc ggccacaaag agatgggccg | 480 |
| gccttgagag cgactgccat gatcaattac gccaactggc ttattgcaaa tggacaggct | 540 |
| tcactcgcca attcgatcgt ctggccgatc gtccagaatg atctctccta cgtcagccag | 600 |
| tactggaatc agagtaccct tgacctttgg gaggaaatcg acagctcctc cttcttcacg | 660 |
| acggctgtgc agcaccgtgc tcttgttgag ggctctgctc tggcaaaaaa gcttggccat | 720 |
| acctgctcaa actgcgactc tcaagcaccg cttgtcttgt gtttcctgca atcctactgg | 780 |
| accggttcct atattctttc caacaccgga ggcggacgtt ccggaaagga cgccaactcc | 840 |
| ctacttggaa gtattcatac ttttgaccca gcagcggcgg gatgcgacga caccactttc | 900 |
| cagccttgct ctgcccgagc cctagcgaac acaaggtcg tcaccgactc gttccgttca | 960 |
| atctactcaa tcaactcggg catcccacag ggccaagcag tcgccgtggg tcgctaccct | 1020 |
| gaagatgtat atcagggcgg aaacgcatgg tatctctgca ccctcgctgc tgcagagcag | 1080 |
| ctgtacgacg cactctatca gtggaacagg atcggatctc tcacgatcac ggacgtcagc | 1140 |
| ttggcattct tccaggatct ctacccatcg gcggcaacag gcacttattc ctcatcctcg | 1200 |
| tcgacctacc aatccatcgt tgccgctgtc aagacgtacg cggacggata catgagcatt | 1260 |
| gttcaaaaat acacccctc caacggcgcc ctcgccgagc agttctcccg caacgatggc | 1320 |
| tccccctct cagccgtcga cctaacctgg tcctacgcct ccctgctcac tgccgccgcg | 1380 |
| cgcagaaatt tctccgtccc cgcctactcc tggggcgaag ccagcgccaa caccgtccca | 1440 |
| tcgtcttgct cggcctcgtc tgcctcaggc ccctgtgcca ccgcgaccaa cacgaactgg | 1500 |
| cccgcaccca catgcaccctc gccaccggca acgtggccg tccgattcaa cgagatggtc | 1560 |
| actaccaact ttggagagaa cgtctttgtc gtgggctcga tcgccgcgtt gggatcttgg | 1620 |
| agtcctagtt ccgctatccc gtgtagcgcg gccgaataca actcacagac gccgttgtgg | 1680 |
| tattgtatcg tgacgttgcc ggcgggcacg agcttccagt ataagtatat caagaaagag | 1740 |
| ccggatggca gtgtggtctg ggagagtgat ccgaacaggt cctatacggt gcctcaaggg | 1800 |
| tgtggcgtga cgactgcgac ggtgaatgat agttggaggt ag | 1842 |

<210> SEQ ID NO 7
<211> LENGTH: 1842
<212> TYPE: DNA
<213> ORGANISM: Artificial Sequence
<220> FEATURE:
<223> OTHER INFORMATION: The sequence is synthesized.

<400> SEQUENCE: 7

| | | | | | |
|---|---|---|---|---|---|
| atgcagtacc | ttcttaaaac | taccctcggc | gctctgagcg | ttgctcagct | tgtcatcgcg | 60 |
| gcaccacatc | ccacggaact | tctccctcgg | gcatcaggt | ccctggattc | atggctttcc | 120 |
| accgaagttc | cttacgctct | cgatggtgta | ttgaacaaca | tcggacccaa | tggtgcaaag | 180 |
| gcccagggg | ccagctccgg | cattgtggtt | gcaagcccca | gcacaagtaa | tcctgactac | 240 |
| ttctactctt | ggactcggga | cgctgcgctc | accatcaaat | gcctgatcga | tgagttcatc | 300 |
| tcgactgggg | atgcgaacct | ggagtcggtg | attcagaact | atatcagctc | ccaggccttc | 360 |
| ttgcaaacag | tgtccaaccc | ctctggcggc | ctgtgtactg | gaggtctcgg | cgagcccaag | 420 |
| tttgaggtca | atgaggcggc | atttactggt | gcttggggcc | ggccacaaag | agatgggccg | 480 |
| gccttgagag | cgactgccat | gatcaattac | gccaactggc | ttattgcaaa | tggacaggct | 540 |
| tcactcgcca | attcgatcgt | ctggccgatc | gtccagaatg | atctctccta | cgtcagccag | 600 |
| tactggaatc | agagtacctt | tgacctttgg | gaggaaatcg | acagctcctc | cttcttcacg | 660 |
| acggctgtgc | agcaccgtgc | tcttgttgag | ggctctgctc | tggcaaaaaa | gcttggccat | 720 |
| acctgctcaa | actgcgactc | tcaagcaccg | cttgtcttgt | gtttcctgca | atcctactgg | 780 |
| accggttcct | atattctttc | caacaccgga | ggcggacgtt | ccggaaagga | cgccaactcc | 840 |
| ctacttggaa | gtattcatac | ttttgaccca | gcagcggcgg | gatgcgacga | caccactttc | 900 |
| cagccttgct | ctgcccgagc | cctagcgaac | cacaaggtcg | tcaccgactc | gttccgttca | 960 |
| atctactcaa | tcaactcggg | catcccacag | ggccaagcag | tcgccgtggg | tcgctaccct | 1020 |
| gaagatgtat | atcagggcgg | aaacgcatgg | tatctctgca | ccctcgctgc | tgcagagcag | 1080 |
| ctgtacgacg | cactctatca | gtggaacagg | atcggatctc | tcacgatcac | ggacgtcagc | 1140 |
| ttggcattct | tccaggatct | ctacccatcg | gcggcaacag | gcacttattc | ctcatcctcg | 1200 |
| tcgacctacc | aatccatcgt | tgccgctgtc | aagacgtacg | cggacggata | catgagcatt | 1260 |
| gttcaaaaat | acaccccttc | caacggcgcc | ctcgccgagc | agttctcccg | caacgatggc | 1320 |
| tcccccctct | cagccgtcga | cctaacctgg | tcctacgcct | ccctgctcac | tgccgccgcg | 1380 |
| cgcagaaatt | tctccgtccc | cgcctactcc | tggggcgaag | ccagcgccaa | caccgtccca | 1440 |
| tcgtcttgct | cggcctcgtc | tgcctcaggc | ccctgtgcca | ccgcgaccaa | cacgaactgg | 1500 |
| cccgcaccca | catgcacctc | gccaccggca | aacgtggccg | tccgattcaa | cgagatggtc | 1560 |
| actaccaact | ttggagagaa | cgtctttgtc | gtgggctcga | tcgccgcgtt | gggatcttgg | 1620 |
| agtcctagtt | ccgctatccc | gtgtagcgcg | gccgaataca | actcacagac | gccgttgtgg | 1680 |
| tattgtatcg | tgacgttgcc | ggcgggcacg | agcttccagt | ataagtatat | caagaaagag | 1740 |
| ccggatggca | gtgtggtctg | ggagagtgat | ccgaacaggt | cctatacggt | gcctcaaggg | 1800 |
| tgtggcgtga | cgactgcgac | ggtgaatgat | agttggaggt | ag | | 1842 |

<210> SEQ ID NO 8
<211> LENGTH: 1839
<212> TYPE: DNA
<213> ORGANISM: Artificial Sequence
<220> FEATURE:
<223> OTHER INFORMATION: The sequence is synthesized.

<400> SEQUENCE: 8

```
atgcagtacc ttcttaaaac taccctcggc gctctgagcg ttgctcagct tgtcatcgcg      60
gcaccacatc ccacggaact tctccctcgg gcatcagggt ccctggattc atggctttcc     120
accgaagttc cttacgctct cgatggtgta ttgaacaaca tcggacccaa tggtgcaaag     180
gcccaggggg ccagctccgg cattgtggtt gcaagcccca gcacaagtaa tcctgactac     240
ttctactctt ggactcggga cgctgcgctc accatcaaat gcctgatcga tgagttcatc     300
tcgactgggg atgcgaacct ggagtcggtg attcagaact atatcagctc ccaggccttc     360
ttgcaaacag tgtccaaccc ctctggcggc ctgtgtactg gaggtctcgg cgagcccaag     420
tttgaggtca atgaggcggc atttactggt gcttggggcc ggccacaaag agatgggccg     480
gccttgagag cgactgccat gatcaattac gccaactggc ttattgcaaa tggacaggct     540
tcactcgcca attcgatcgt ctggccgatc gtccagaatg atctctccta cgtcagccag     600
tactggaatc agagtacctt tgacctttgg gaggaaatcg acagctcctc cttcttcacg     660
acggctgtgc agcaccgtgc tcttgttgag ggctctgctc tggcaaaaaa gcttggccat     720
acctgctcaa actgcgactc tcaagcaccg cttgtcttgt gtttcctgca atcctactgg     780
accggttcct atattctttc caacaccgga ggcggacgtt ccggaaagga cgccaactcc     840
ctacttggaa gtattcatac ttttgaccca gcagcggcgg gatgcgacga caccactttc     900
cagccttgct ctgcccgagc cctagcgaac cacaaggtcg tcaccgactc gttccgttca     960
atctactcaa tcaactcggg catcccacag ggccaagcag tcgccgtggg tcgctacccet    1020
gaagatgtat atcagggcgg aaacgcatgg tatctctgca ccctcgctgc tgcagagcag    1080
ctgtacgacg cactctatca gtggaacagg atcggatctc tcacgatcac ggacgtcagc    1140
ttggcattct tccaggatct ctacccatcg gcggcaacag gcacttattc ctcatcctcg    1200
tcgacctacc aatccatcgt tgccgctgtc aagacgtacg cggacggata catgagcatt    1260
gttcaaaaat acaccccttc caacggcgcc ctcgccgagc agttctcccg caacgatggc    1320
tccccctct cagccgtcga cctaacctgg tcctacgcct ccctgctcac tgccgccgcg    1380
cgcagaaatt tctccgtccc cgatccatgg ggcgaagcca gcgccaacac cgtcccatcg    1440
tcttgctcgg cctcgtctgc ctcaggcccc tgtgccaccg cgaccaacac gaactggccc    1500
gcacccacat gcacctcgcc accggcaaac gtggccgtcc gattcaacga tggtcact     1560
accaactttg gagagaacgt ctttgtcgtg ggctcgatcg ccgcgttggg atcttggagt    1620
cctagttccg ctatcccgtg tagcgcggcc gaatacaact cacagacgcc gttgtggtat    1680
tgtatcgtga cgttgccggc gggcacgagc ttccagtata gtatatcaa gaaagagccg     1740
gatggcagtg tggtctggga gagtgatccg aacaggtcct atacggtgcc tcaagggtgt    1800
ggcgtgacga ctgcgacggt gaatgatagt tggaggtag                           1839
```

<210> SEQ ID NO 9
<211> LENGTH: 26
<212> TYPE: DNA
<213> ORGANISM: Artificial Sequence
<220> FEATURE:
<223> OTHER INFORMATION: The sequence is synthesized.

<400> SEQUENCE: 9

```
ctctggcggc ctgtgtactg gaggtc                                           26
```

```
<210> SEQ ID NO 10
<211> LENGTH: 27
<212> TYPE: DNA
<213> ORGANISM: Artificial Sequence
<220> FEATURE:
<223> OTHER INFORMATION: The sequence is synthesized.

<400> SEQUENCE: 10
acacaggccg ccagaggggt tggacac                                         27

<210> SEQ ID NO 11
<211> LENGTH: 28
<212> TYPE: DNA
<213> ORGANISM: Artificial Sequence
<220> FEATURE:
<223> OTHER INFORMATION: The sequence is synthesized.

<400> SEQUENCE: 11
ctgcctcagg cccctgtgcc accgcgac                                        28

<210> SEQ ID NO 12
<211> LENGTH: 27
<212> TYPE: DNA
<213> ORGANISM: Artificial Sequence
<220> FEATURE:
<223> OTHER INFORMATION: The sequence is synthesized.

<400> SEQUENCE: 12
acaggggcct gaggcagacg aggccga                                         27

<210> SEQ ID NO 13
<211> LENGTH: 29
<212> TYPE: DNA
<213> ORGANISM: Artificial Sequence
<220> FEATURE:
<223> OTHER INFORMATION: The sequence is synthesized.

<400> SEQUENCE: 13
agttccgcta tcccgtgtag cgcggccga                                       29

<210> SEQ ID NO 14
<211> LENGTH: 28
<212> TYPE: DNA
<213> ORGANISM: Artificial Sequence
<220> FEATURE:
<223> OTHER INFORMATION: The sequence is synthesized.

<400> SEQUENCE: 14
acacgggata gcggaactag gactccaa                                        28

<210> SEQ ID NO 15
<211> LENGTH: 28
<212> TYPE: DNA
<213> ORGANISM: Artificial Sequence
<220> FEATURE:
<223> OTHER INFORMATION: The sequence is synthesized.

<400> SEQUENCE: 15
cgccgttgtg gtattgtatc gtgacgtt                                        28

<210> SEQ ID NO 16
<211> LENGTH: 27
<212> TYPE: DNA
<213> ORGANISM: Artificial Sequence
<220> FEATURE:
<223> OTHER INFORMATION: The sequence is synthesized.
```

```
<400> SEQUENCE: 16
acaataccac aacggcgtct gtgagtt                                              27

<210> SEQ ID NO 17
<211> LENGTH: 27
<212> TYPE: DNA
<213> ORGANISM: Artificial Sequence
<220> FEATURE:
<223> OTHER INFORMATION: The sequence is synthesized.

<400> SEQUENCE: 17
tggggatgcg aacctggagt cggtgat                                              27

<210> SEQ ID NO 18
<211> LENGTH: 26
<212> TYPE: DNA
<213> ORGANISM: Artificial Sequence
<220> FEATURE:
<223> OTHER INFORMATION: The sequence is synthesized.

<400> SEQUENCE: 18
tccaggttcg catccccagt cgagat                                               26

<210> SEQ ID NO 19
<211> LENGTH: 29
<212> TYPE: DNA
<213> ORGANISM: Artificial Sequence
<220> FEATURE:
<223> OTHER INFORMATION: The sequence is synthesized.

<400> SEQUENCE: 19
atttctccgt ccccgatcca tggggcgaa                                            29

<210> SEQ ID NO 20
<211> LENGTH: 29
<212> TYPE: DNA
<213> ORGANISM: Artificial Sequence
<220> FEATURE:
<223> OTHER INFORMATION: The sequence is synthesized.

<400> SEQUENCE: 20
atggatcggg gacggagaaa tttctgcgc                                            29
```